United States Patent
Alhakamy et al.

(10) Patent No.: US 11,497,765 B1
(45) Date of Patent: Nov. 15, 2022

(54) THIOCTAMER EXPEDITES WOUND HEALING

(71) Applicant: King Abdulaziz University, Jeddah (SA)

(72) Inventors: Nabil A. Alhakamy, Jeddah (SA); Usama A. Fahmy, Jeddah (SA); Osama A. A. Ahmed, Jeddah (SA); Basma G. Eid, Jeddah (SA); Mohammed Z. Nasrullah, Jeddah (SA); Ashraf B. Abdel-naim, Jeddah (SA); Amgad Khedr, Jeddah (SA); Gamal A. Mohamed, Jeddah (SA); Mohamed W. Alrabei, Jeddah (SA); Sabrin R. M. Ibrahim, Jeddah (SA)

(73) Assignee: KING ABDULAZIZ UNIVERSITY, Jeddah (SA)

(*) Notice: Subject to any disclaimer, the term of this patent is extended or adjusted under 35 U.S.C. 154(b) by 0 days.

(21) Appl. No.: 17/681,794

(22) Filed: Feb. 27, 2022

(51) Int. Cl.
| | |
|---|---|
| *A61K 31/785* | (2006.01) |
| *A61K 47/54* | (2017.01) |
| *A61P 17/02* | (2006.01) |
| *A61K 9/06* | (2006.01) |
| *A61K 9/00* | (2006.01) |
| *A61K 9/14* | (2006.01) |

(52) U.S. Cl.
CPC .......... *A61K 31/785* (2013.01); *A61K 9/0014* (2013.01); *A61K 9/06* (2013.01); *A61K 9/14* (2013.01); *A61K 47/545* (2017.08); *A61P 17/02* (2018.01)

(58) Field of Classification Search
None
See application file for complete search history.

(56) References Cited

U.S. PATENT DOCUMENTS

| | | |
|---|---|---|
| 2006/0122113 A1 | 6/2006 | Pinchasi et al. |
| 2010/0196317 A1 | 8/2010 | Forte et al. |
| 2014/0056848 A1 | 2/2014 | Mak et al. |
| 2015/0224163 A1 | 8/2015 | Walsh |
| 2016/0338993 A1 | 11/2016 | Martins-Green et al. |
| 2017/0246090 A1 | 8/2017 | Briand et al. |
| 2021/0260199 A1 | 8/2021 | Song et al. |

OTHER PUBLICATIONS

Swezey, "The Difference Between Acute and Chronic Wounds", https://www.woundsource.com/blog/difference-between-acute-and-chronic-wounds, accessed Jun. 9, 2022 (Year: 2022).*
Flen Health, "Acute & chronic wounds", https://www.flenhealth.com/patients/disease-awareness/acute-chronic-wounds, accessed Jun. 9, 2022 (Year: 2022).*
Alleva et al. "alpha-Lipoic acid supplementation inhibits oxidative damage, accelerating chronic wound healing in patients undergoing hyperbaric oxygen therapy" 2005.
Chen et al. "Tannic acid-thioctic acid hydrogel: a novel injectable supramolecular adhesive gel for wound healing" 2021.
Jayaraj et al. "A pre-formulation strategy for the liposome encapsulation of new thioctic acid conjugates for enhanced chemical stability and use as an efficient drug carrier for MPO-mediated atherosclerotic CVD treatment" 2020.
Külkamp-Guerreiro et al. "Evaluation of lipoic acid topical application on rats skin wound healing" 2013.
Stevens et al. "Alpha Lipoic Acid Restores Skin Wound Healing Capacity in Streptozotocin-Induced Diabetes" 2005.

* cited by examiner

*Primary Examiner* — Melissa L Fisher
(74) *Attorney, Agent, or Firm* — WC&F IP

(57) ABSTRACT

Thioctamer, a nanoconjugate of glatiramer acetate (GA) and thioctic acid (TA), e.g. in the form of nanospheres, is provided as are compositions comprising thioctamer and methods of using the same for wound healing. Application of thioctamer to a wound accelerates wound healing, compared to control wounds that are not treated with the copolymer.

6 Claims, 5 Drawing Sheets

THIOCTAMER EXPEDITES WOUND HEALING

BACKGROUND OF THE INVENTION

Technical Field

The disclosure generally relates to improved compositions and methods of wound healing and closure. In particular, the disclosure provides thioctamer, a nanoconjugate of glatiramer acetate (GA) and thioctic acid (TA, also known as "lipoic acid") and methods of its use to accelerate wound healing.

Description of Related Art

Diabetes mellitus (DM) plagues many nations worldwide. The cause of this noninfectious chronic disease is pancreas failure to successfully produce sufficient insulin or the body's inability to effectively utilize insulin. It is expected that diabetes will become most prevalent in MENA (North Africa and Middle East) because of speedy economic development, urbanization as well as changes in how people live in the region. It is estimated by International Diabetes Federation (IDF) that in 2019, 55 million adults between ages 20 and 79 have diabetes in the MENA Region. Further, the IDF estimates a rise in this figure to 108 million by 2045. Hyperglycemia affects about 11% of live births in the MENA Region in pregnancy. The number of adults having diabetes in Saudi Arabia alone is 4,275,200. The WHO (World Health Organization) reports that Saudi Arabia is second in list of countries where diabetes is prevalent in the Middle East region and is seventh worldwide.

Diabetes brings about a number of acute complications such as cardiovascular diseases, cerebrovascular diseases, renal disorders as well as obesity. Likewise, people with diabetes experience impairment when it comes to healing of serious wounds. Such individuals are susceptible to, for example, the development of acute non-healing diabetic foot ulcers (DFUs).

From the time of Hippocrates, wound healing has been deemed important. Wound healing is modulated by several mechanisms and physiological processes. The process is complex as it consists of a variety of interdependent stages, which include hemostasis, inflammation, proliferation, and remodeling. When an individual is wounded, the initial phase of hemostasis starts instantly, by vascular constriction and formation of a fibrin clot. Pro-inflammatory cytokines and growth factors are produced by the clot and surrounding wound tissue. After bleeding is controlled, inflammatory cells migrate into the wound (chemotaxis) and facilitate an inflammatory phase, involving sequential entry of neutrophils, macrophages and lymphocytes. This is usually followed by the proliferative phase, overlapping with the inflammatory phase. This involves epithelial proliferation and movement above the provisional matrix in the wound, known as re-epithelialization. The final remodeling sets in and it is possible to continue for years. It is characterized by regression of numerous newly produced capillaries and progresses towards returning the wound's vascular density to normal. However, this normal wound healing process is less efficient and may not function at all, or may take a very long time, in certain subjects, e.g. the elderly and those with diabetes.

There is a need in the art to provide improved agents to facilitate wound healing, especially in subjects in whom the process is compromised.

Alleva et al. (2005) discloses that lipoic acid (LA) supplementation efficiently reduced both the lipid and DNA oxidation induced by oxygen exposure during wound healing by directly interacting with free radicals or by recycling vitamin E. An inhibitory effect of LA on the pro-inflammatory cytokine interleukin-6 was observed. Taken together, the authors conclude that LA could have an adjuvant effect in HBO therapy which is used for impaired wound healing treatment. However, glatiramer acetate is not mentioned.

Chen et al. (2021) discloses a tannic acid-thioctic acid (TATA) supramolecular hydrogel. The TATA hydrogel was used as an adhesive for skin wound healing and exhibited decreased therapeutic time and an enhanced regeneration effects compared with suture treatment. This hydrogel also showed antibacterial activity in a burn wound infection model. The authors concluded that the TATA hydrogel exhibits potential as a surgical antibacterial bioadhesive for a broad range of medical applications. However, glatiramer acetate is not mentioned.

Jayaraj et al. (2020) disclose lipoyl-apocynin and lipoyl-sesamol bio-active conjugates of thioctic acid (also known as alpha-lipoic acid). However, glatiramer acetate is not mentioned nor is the treatment of wounds.

Külkamp-Guerreiro et al. (2013) evaluated the effects of lipoic acid (thioctic acid) topical application on wound healing on rat skin, and the consequences of lipoic acid nanoencapsulation on this process. The results showed that the topical application of lipoic acid improved wound healing. On the seventh day after surgery, animals treated with lipoic acid showed an increased healing rate (60.7±8.4%) compared to the negative control group (43.0±17.4%). Nanoencapsulation of the lipoic acid reversed the pro-oxidant activity and diminished wound repair. However, glatiramer acetate is not mentioned.

Stevens et al. (2005) discloses the use of alpha lipoic acid (ALA) to treat wounds in diabetic rats. The results showed that the wounds of diabetic rats healed at the same rate as nondiabetic animals and were completely closed after 8 days. The authors conclude that antioxidant therapy accelerates wound healing in experimental diabetes and that in patients with diabetes, prophylactic use of ALA might be useful in preventing the development of non-healing skin ulcers. However, glatiramer acetate is not mentioned.

U.S. patent application Ser. No. 20210260199 discloses conjugated naringenin and lipoic acid which are linked with a linker. However, glatiramer acetate, hydrogels and wounds are not mentioned.

U.S. patent application Ser. No. 20160338993 discloses method of treating a chronic wound in a subject in need thereof by administering to the subject at least one antioxidant agent. In some aspects, the antioxidant agent is lipoic acid. However, glatiramer acetate is not mentioned, nor are conjugated molecules nor hydrogels.

U.S. patent application Ser. No. 20170246090 describes a topical composition that forms a liquid crystals gel network. The system comprises a) at least one type of emulsifier having an enzyme cleavable bound, b) at least one emollient, c) at least one polar solvent, d) at least one active ingredient, e) water. The active ingredient may be lipoic acid (see claim 13) or glatiramer acetate (see claim 18). However, the two are not described as being present in the same preparation, the composition is not for wound healing and hydrogels and conjugation are not discussed.

U.S. patent application Ser. No. 20150224163 provides a method of preventing and/or treating noise-induced auditory impairments which includes administration of an effective amount of glatiramer acetate or a derivative thereof. The derivative can be any salt, ester, ether, polymorph, metabolite, pure form, particle, isomer, mixture of isomers, complex, or combination thereof provided it maintains the function of GA. However, lipoic acid is not referred to nor is the treatment of wounds.

U.S. patent application Ser. No 20140056848 discloses compositions for treating a subject with multiple sclerosis. The compositions include a therapeutically effective amount of 2ME2 or a derivative thereof and may comprise a second agent, which may be glatiramer acetate (claim 9) or lipoic acid (claim 10). However, the treatment of wounds is not mentioned, the lipoic acid and glatiramer acetate are not listed as present in the same composition, and their conjugation is not mentioned.

U.S. patent application Ser. No. 20100196317 teaches methods for treating multiple sclerosis by administering a cyclosporin compound. A second active agent such as lipoic acid or glatiramer acetate may also be administered (see claims 12 and 13). However, there is no suggestion of administering the two together, conjugating the two or treating wounds.

U.S. patent application 20060122113 discloses compositions comprising a mixture of polypeptides, wherein each polypeptide (a) is a copolymer of the amino acids L-glutamic acid, L-alanine, L-tyrosine, and L-lysine. A second active agent such as lipoic acid or glatiramer acetate may also be on the compositions. The compositions are used to promote nerve regeneration e.g. after blunt trauma such as a gunshot wound. However, there is no discussion of conjugating active agents, hydrogels are not mentioned and wounds in general are not treated.

SUMMARY OF THE INVENTION

Other features and advantages of the present invention will be set forth in the description of invention that follows, and in part will be apparent from the description or may be learned by practice of the invention. The invention will be realized and attained by the compositions and methods particularly pointed out in the written description and claims hereof.

"Thioctamer" is a nanoconjugate of glatiramer acetate (GA) and thioctic acid (TA, also known as "lipoic acid", LA). A formulation of thioctamer loaded hydrogel was tested and found to have efficacy in expediting wound healing in a rat model of diabetic wounds, compared to GA or TA alone. Particle size, zeta potential and the ability to speed wound healing was assessed. Histopathological and immunohistochemical assessments of the inflammation markers IL-6 and TNF-α were performed. The results showed that thioctamer had a particle size of 137±21.4 nm with polydispersity index (PDI) of 0.235 and a positive zeta potential value of 7.43±4.95 mV. At day 7, wounds of diabetic rats to which thioctamer preparation was administered showed almost complete healing (95.6±8.6%) whereas animals treated with TA or GA alone exhibited healing of only 56.5±5.8% and 62.6±7.1%, respectively. A low level of inflammatory cells was observed in thioctamer treated rats; thioctamer significantly ($P<0.05$) inhibited IL-6 and TNF-α expression as compared to sections obtained from the negative control, TA, GA or positive control group animals at day 7. Thioctamer is thus an improved treatment for wound healing It is an object of this disclosure to provide thioctamer nanospheres comprised of conjugated glatiramer acetate (GA) and thioctic acid (TA), wherein the thioctamer nanospheres have a size of from 115-160 nm.

It is an object of this disclosure to provide a hydrogel comprising the thioctamer nanospheres comprised of conjugated glatiramer acetate (GA) and thioctic acid (TA), wherein the thioctamer nanospheres have a size of from 115-160 nm.

It is a further object to provide a dehydrated hydrogel preparation comprising thioctamer nanospheres comprised of conjugated glatiramer acetate (GA) and thioctic acid (TA), wherein the thioctamer nanospheres have a size of from 115-160 nm.

This disclosure also provides a method of treating a wound in a subject in need thereof, comprising applying to the wound a therapeutically effective amount of thioctamer nanospheres comprised of glatiramer acetate (GA) and thioctic acid (TA) and having a size of from 115-160 nm, thereby treating the wound. In some aspects, the thioctamer nanospheres are present in a pharmaceutical formulation comprising at least one physiologically acceptable carrier. In some aspects, the pharmaceutical formulation is a hydrogel. In further aspects, the wound is an acute wound. In additional aspects, the wound is a chronic wound. In additional aspects, the subject is diabetic. In yet further aspects, the wound is a diabetic ulcer. In alternative aspects, the step of applying results in acceleration of one or more of: closure of the wound, re-epithelization of the wound, keratinization of the wound, generation of mature organized tissue with a characteristic perpendicular arrangement of newly produced blood capillaries and a reduction of inflammatory cells in or at the wound site, compared to a control wound that is not treated with the thioctamer nanospheres.

Also provided is a method of making thioctamer nanospheres comprising: forming a first solution comprising glatiramer acetate (GA); forming a second solution comprising thioctic acid (TA); combining the first solution and the second solution under conditions that permit the GA and TA to react and form thioctamer nanospheres. In some aspects, the GA and the TA are reacted at a molar ratio of 1:1. In other aspects, the methods further comprises a step of isolating the thioctamer nanospheres. In yet further aspects, the method further comprises a step of dehydrating the thioctamer nanospheres.

DETAILED DESCRIPTION

Figure 1A:
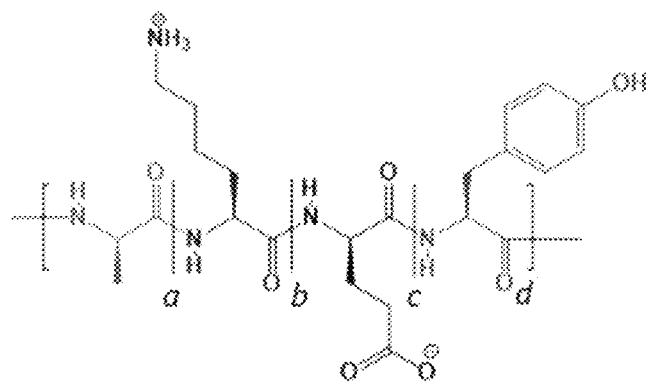
FIGS. 1A and B. A, schematic chemical structure of GA showing the four constituent amino acids, L-alanine, and L-lysine, L-glutamic acid, L-tyrosine; a, b, c and d refer to molar concentrations of the four amino acids, for example, 0.427, 0.338, 0.141 and 0.095, respectively. The amino acids do not necessarily occur in the order depicted in A. B, chemical structure of TA.

Glatiramer acetate (GA) (IUPAC designation [L-alanine compound with L-tyrosine compound with L-lysine compound with L-glutamic acid acetic acid]) is a random, inherently complex polymeric synthetic polypeptide (protein) composed of four different naturally occurring amino acids: L-alanine (Ala), L-lysine (Lys), L-glutamic acid (Glu) and L-tyrosine (Tyr). An exemplary structure is shown in FIG. 1A. According to some sources, the four amino acids are present in the polymer at defined molar ratios: [L-alanine (0.427), L-lysine (0.338), L-glutamic acid (0.141) and L-tyrosine (0.095)], giving GA amphipathic properties. However, those rations may vary e.g. by up to about 10%-20%, i.e. to be about 10% to 20% more or less for each amino acid. GA is manufactured by copolymerizing the four amino acids. The overall process results in high molecular weight intermediates which are subsequently depolymerized and purified to result in the final product. The final product is a polymer mixture and exhibits variability in molecular weight distribution. The average length of the polypeptide chains is about 60 residues and the average molecular weight is approximately 10 kDa, with a range of from 2.5 to >20 kDa. Most GA falls in the range of from about 5-9 KDa.

GA, also known Copolymer-1 (Cop-1; FIG. 1A), is certified in a number of countries for multiple sclerosis (MS) treatment (e.g. COPAXONE®). It was officially approved in 1996 by the US FDA (United States Food and Drug Administration) and in 2001 by the EMA (European Medicines Agency). is used for treating relapsing-remitting multiple sclerosis (RRMS), a central nervous system (CNS) inflammatory disease that damages the myelin sheath. The basic cationic amino acid residue lysine appears to be necessary for GAs therapeutic effect.

Figure 1B:
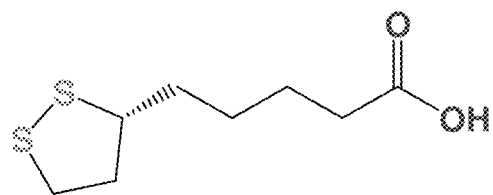

The present disclosure provides a novel co-polymer, referred to herein as "Thioctamer", which comprises GA copolymerized with thioctic acid (Alpha-lipoic acid, TA). TA is an oil and water soluble organo-sulfur metabolite that possesses two thiol groups (FIG. 1B). The carbon atom at C6 is chiral and the molecule exists as two enantiomers (R)-(+)-lipoic acid (RLA) and (S)-(-)-lipoic acid (SLA) and as a racemic mixture (R/S)-lipoic acid (R/S-LA). Only the (R)-(+)-enantiomer (RLA) exists in nature and this form is preferred for use in the present compositions and methods. However, either or both of the racemate and the RLA can be used. RLA is biosynthesized by animals, plants, and humans and can be isolated from natural sources. However, RLA can also be chemically synthesized, and chemical synthesis is generally used as the source for drug manufacturing processes such as those used herein. It is used e.g. in supplements and foods and displays diverse bio-activities and appears to function as an antioxidant, immuno-modulatory, anti-cancer, anti-aging, anti-inflammatory, antiviral, and neuroprotective agent. It improves utilization of glucose and boosts production of insulin, hence ameliorating hyperglycemia-induced oxidative damage and has been found to reduce and improve diabetes-related disorders such as retinopathy, neuropathy, and autonomic neuropathy.

The present disclosure provides nanoconjugated copolymers of GA and TA in the form of nanospheres, as well as various pharmaceutical formulations of the copolymers and methods of their use. In some aspects, thioctamer nanospheres are formulated as a hydrogel. In further aspects, thioctamer is used to expedite wound healing.

Thioctamer Preparation

Methods of making thioctamer are provided. Thioctamer is prepared by conjugation of GA and TA. Generally, the GA and TA are each dissolved separately in suitable solvents. They may each be dissolved in the same type of solvent or each may be dissolved in a different type of solvent, so long as the two types of solvents are miscible. The dissolved GA and TA are then combined in a reaction medium in a molar ratio ranging from e.g. about 1.5:0.5 GA/TA or vice versa, i.e. about 1.5:0.5 TA to GA, including all decimal fractions in between. In some aspects, the molar ratio is about 1:1, but can vary e.g. by about 10% for either GA or TA.

The reaction media is generally water, such as deionized water. In some aspects, a pH adjustment agent is added, examples of which include but are not limited to triethanolamine, piperidine, pyridine, etc. The desired pH should be in the range of from about pH 6.5 to 7.5. In some aspects, TEA is used to adjust the pH, and the TEA is added in a 1:1 molar ratio of TEA to TA.

The two solutions (GA and TA) are then mixed with agitation, e.g. vortexing for at least about 30 seconds, and usually at least about 1-5 minutes, to allow for thorough mixing and conjugation. The conjugated thioctamer product can be recovered from the reaction mixture and purified (for example, to remove unreacted GA or TA) e.g. by size exclusion chromatography, centrifugation using an ultracentrifuge, by filtration using membrane filters, etc. In some aspects, the product is dehydrated, e.g. by air drying, or by lyophilization, etc. Dehydrated forms may be rehydrated prior to use, e.g. prior to formulation, such as into a usable preparation, especially those suitable for topical application as gels, creams, ointments, sprays, or topical solutions) as described in more detail below. Alternatively, if the purified reaction mixture is suitable for further processing "as is", dehydration may not be necessary.

Once conjugated, the thioctamer generally is in the form of nanospheres (particles) having a size ranging from about 75 to 200 nm, such as from about 100-175 nm, such as from about 115-160 nm, e.g. about 115, 120, 125, 130, 135, 140, 145, 150, 155 or 160 nm. In some aspects, the particle size is about 137±21.4 nm.

Within the thioctamer, the amino acids are generally joined covalently, i.e. by covalent bonding. Upon reaction as described herein, the structure of the GA is not changed. The negative charge of TA interacts with the positive charge of the basic amino acid lysine, lysine contains a positively charged amino on its side-chain that is involved in forming hydrogen bonds with negatively charged non-protein atoms (e.g. TA). Generally, the thioctamer intercalates within the particles that are formed.

Formulations

The complexes of the present disclosure may be given in the form of topical solutions, suspensions, etc. and are applied to and/or around the affected areas (a wound). Other excipients which are normally added to such formulations can be included in the present compositions. In one embodiment, the topical formulation may take the form of a cream, a lotion, an ointment, a hydrogel, a colloid (e.g. hydrocolloid), a gel (e.g. hydrogel), a foam, an oil, a milk, a suspension, a wipe, a sponge, a solution, an emulsion, a paste, a patch, a pladget, a swab, a dressing, a bandage, a spray, a film, a pad, a dressing containing silver or alginates, a gauze dressing, etc. In some aspects, the topical formulation are provided as a hydrogel formulation.

Alternatively, the conjugate may be dehydrated and used as a solid powder or in a pulverized form that is applied directly to a wound.

The topical formulation may comprise one or more pharmaceutically acceptable carriers, and the carriers may be solid (e.g., a paste or wipe), or a fluid (e.g., gel or ointment). Examples of the pharmaceutically acceptable carriers that are usable in the context of the present disclosure include carrier materials such as a solvent, a stabilizer, a solubilizer, a filler, a tonicity enhancing agent, a structure-forming agent, a suspending agent, a dispersing agent, a chelating agent, an emulsifying agent, an anti-foaming agent, an ointment base, an emollient, a skin protecting agent, a gel-forming agent, a thickening agent, a pH adjusting agent, a preservative, a penetration enhancer, a complexing agent, a lubricant, a demulcent, a viscosity enhancer, a bioadhesive polymer, or a combination thereof. Examples of solvents are water or purified water, alcohols (e.g., ethanol, benzyl alcohol), vegetable, marine and mineral oils, polyethylene glycols, propylene glycols, glycerol, and liquid polyalkylsiloxanes. Inert diluents or fillers may be included in the composition, such as, sucrose, sorbitol, sugar, mannitol, microcrystalline cellulose, starches, calcium carbonate, sodium chloride, lactose, calcium phosphate, calcium sulfate, or sodium phosphate. Buffering agents may be included in the composition. Examples of buffering agents include citric acid, acetic acid, lactic acid, hydrogenophosphoric acid, diethylamine, sodium hydroxide and tromethane (i.e., tris(hydroxymethyl)aminomethane hydrochloride). Other ingredients which may be included in the compositions include suspension agents. Suitable suspending agents are, for example, naturally occurring gums (e.g., acacia, arabic, xanthan, and tragacanth gum), celluloses (e.g., carboxymethyl-, hydroxyethyl-, hydroxypropyl-, and hydroxypropylmethyl-cellulose), alginates and chitosans.

Examples of dispersing or wetting agents that may be included in the compositions are naturally occurring phosphatides (e.g., lecithin or soybean lecithin), condensation products of ethylene oxide with fatty acids or with long chain aliphatic alcohols (e.g., polyoxyethylene stearate, polyoxyethylene sorbitol monooleate, and polyoxyethylene sorbitan monooleate). Preservatives may be added to a topical composition to prevent, for example, microbial contamination that can affect the stability of the formulation and/or cause infection in the patient. Suitable examples of preservatives include parabens (such as methyl, ethyl, propyl, /p-hydroxybenzoate, butyl, isobutyl, and isopropylparaben), potassium sorbate, sorbic acid, benzoic acid, methyl benzoate, phenoxyethanol, bronopol, bronidox, MDM hydantoin, iodopropynyl butylcarbamate, benzalconium chloride, cetrimide, and benzylalcohol. Examples of chelating agents that may be included in the compositions include sodium EDTA and citric acid.

Examples of gel bases or viscosity-increasing agents that may be included in the topical compositions include liquid paraffin, polyethylene, fatty oils, colloidal silica or aluminum, glycerol, propylene glycol, propylene carbonate, carboxyvinyl polymers, magnesium-aluminum silicates, hydrophilic polymers (such as, for example, starch or cellulose derivatives), water-swellable hydrocolloids, carragenans, hyaluronates, alginates, and acrylates. Ointment bases suitable for use in the compositions of the present disclosure may be hydrophobic or hydrophilic, and include paraffin, lanolin, liquid polyalkylsiloxanes, cetanol, cetyl palmitate, vegetal oils, sorbitan esters of fatty acids, polyethylene glycols, and condensation products between sorbitan esters of fatty acids, ethylene oxide (e.g., polyoxyethylene sorbitan monooleate), polysorbates, white petrolatum and white wax. Examples of humectants that may be included in the compositions are ethanol, isopropanol glycerin, propylene glycol, sorbitol, lactic acid, and urea. Suitable emollients include cholesterol and glycerol. Examples of skin protectants that may be included in the compositions include vitamin E, allatoin, glycerin, zinc oxide, vitamins, and sunscreen agents.

Thickening agents are generally used to increase viscosity and improve bioadhesive properties of pharmaceutical or cosmetic compositions. These agents may be used in some embodiments of the present disclosure. Examples of thickening agents include, but are not limited to, celluloses, polyethylene glycol, polyethylene oxide, naturally occurring gums, gelatin, karaya, pectin, alginic acid, povidone, and CARBOPOL™ polymers. In some aspects, the thickening agents have thixotropic properties (i.e., agents whose viscosity is decreased by shaking or stirring). The presence of such an agent in a composition allows the viscosity of the composition to be reduced at the time of administration to facilitate its application to the skin and, to increase after application so that the composition remains at the site of administration. Bioadhesive polymers maybe used in various embodiments (e.g., on a bandage, in a gel, etc.) are useful to hydrate the skin and enhance its permeability. Bioadhesive polymers can also function as thickening agents. Examples of bioadhesive polymers include, but are not limited to, pectin, alginic acid, chitosan, polysorbates, poly(ethyleneglycol), oligosaccharides and polysaccharides, cellulose esters and cellulose ethers, and modified cellulose polymers.

Permeation enhancing agents are vehicles containing specific agents that affect the delivery of active components through the skin. Such agents may be employed in various embodiments. Permeation enhancing agents are generally divided into two classes: solvents and surface-active compounds (amphiphilic molecules). Examples of solvent permeation enhancing agents include alcohols (e.g., ethyl alcohol, isopropyl alcohol), dimethyl formamide, dimethyl acetamide, dimethyl sulfoxide, 1-dodecylazocyloheptan-2-one, N-decyl-methylsulfoxide, lactic acid, N,N-diethyl-m-toluamide, N-methyl pyrrolidone, nonane, oleic acid, petrolatum, polyethylene glycol, propylene glycol, salicylic acid, urea, terpenes, and trichloroethanol. Surfactant permeation enhancing agents may be nonionic, amphoteric, cationic, or zwitterionic. Suitable nonioinic surfactants include poly (oxyethylene)-poly(oxypropylene) block copolymers, commercially known as poloxamers; ethoxylated hydrogenated castor oils; polysorbates, such as TWEEN™ 20 or TWEEN™ 80. Amphoteric surfactants include quaternized imidazole derivatives, cationic surfactants include cetypyridinium chloride, and zwitterionic surfactants include the betaines and sulfobetaines. Other examples of suitable permeation enhancers include pentadecalactone, 2-pyrrolidine, 1-dodecal-azacycloheptane-2-one, calcium thioglycolate, hexanol, derivatives of 1,3-dioxanes (i.e., 1,3-dioxacyclohexanes) and 1,3-dioxalanes (i.e., 1,3-dioxacyclopentanes), 1-N-dodecyl-2-pyrrolidone-5-carboxylic acid, 2-pentyl-2-oxo-pyrrolidineacetic acid, 2-dodecyl-2-oxo-1-pyrrolidineacetic acid, and 1-azacycloheptan-2-one-2-dodecylacetic acid among others.

In some aspects, the thioctamer is formulated as a hydroxy propyl methyl cellulose (HPMC) hydrogel in which the amount of HPMC is 1.5% w/v concentration.

One or more topical or local anesthetic agents may also be included in the formulations, examples of which include but are not limited to: lidocaine, benzocaine, dibucaine, novocaine (procaine), pramoxine, phenol, capsaicin, etc. Alternatively, in the context of the methods of treating a wound described herein, one or more anesthetic agents may be applied to the wound as a separate preparation, e.g. before or concomitantly with application of the thioctamer preparation.

In addition, the preparations may include other agents such as growth factors, antibiotics, agents that treat pain, immunomodulating agents, anti-inflammatory agents, angiogenic factors, etc.

The amount of thioctamer that is present in a formulation is generally in the range of from about 1-99%. Preferred preparations of thioctamer contain from about 1 to about 100 mg/g of preparation (such as hydrogel), e.g. from about 5 to 50 or about 10 to 25 mg/g, such as about 10, 11, 12, 13, 14, 15, 16, 17, 18, 18 or 20 mg/g, including all 0.1 decimal fractions in between each integer. In some aspects, the amount is 16.6 mg/g of formulation.

Uses and Methods

It has been found that the application of thioctamer copolymers accelerates or promotes the wound healing and closure process. In some aspects, the acceleration is in comparison to a control wound that is left untreated. In other aspects, the acceleration is in comparison to a control wound that is treated with GA alone or TA alone. The rates of healing, using such markers as wound closure, re-epithelization of the wound, keratinization of the wound, generation of mature organized tissue with a characteristic perpendicular arrangement of newly produced blood capillaries, and a reduction of inflammatory cells in or at the wound, are faster than the controls by from at least about 5 to 50%, such as from at least about 5, 10, 15, 20, 25, 30, 35, 40, 45 or 50%. In some aspects, the healing is from about 30 to 40% faster, e.g. at least about 3, 31, 32, 33, 34, 35, 36, 37, 38, 39, or 40% faster.

Accordingly, methods of treating wounds and/or accelerating wound healing and/or promoting wound healing in a subject in need thereof using the copolymers described herein are provided. Subjects that are treated are generally mammals and may be humans. However, veterinary applications are also encompassed, e.g. the methods are also used for the treatment of companion pets such dogs and cats, service animals, animals residing in protected areas, animals used for food production, commercial animals used e.g. for transportation or sport, etc.

The amount of thioctamer formulation that is applied to a wound will vary, e.g. with the size of the wound and is best determined by a medical professional such as a doctor, nurse practitioner or nurse. Generally, the amount is sufficient to cover the entire surface of the wound and the margins of the wound, and some of the surrounding skin to insure complete coverage.

In some aspects, the wound is a surface wound (e.g. a wound of the skin, or an area that is accessible to topical treatment) and the methods involve topical application of a pharmaceutical compositions comprising thioctamer copolymers to a wound surface. Formulations that are used are e.g. creams, ointments, solutions, eye drops, gels, powders or sprays and may be applied to areas such as the skin, scalp, inside the mouth or throat, in the nose, in the eyes or in the ears. In some aspects, the thioctamer is applied as a hydrogel permeated with the thioctamer.

In other aspects, the wound is an internal wound, such as a wound that is inflicted during surgery or an injury that punctures below the skin. In such cases, the formulation may be e.g. a biodegradable or resorbable matrix or implant that releases the formulation over a period of time to promote healing after the surgical incision or puncture wound is closed.

Wounds that are treated may be acute wounds due to e.g. accidents, such as lacerations, bites, scratches, inadvertent abrasions or scrapes, punctures, avulsions, etc. Alternatively, the acute wounds may be purposefully introduced, e.g. due to surgery, e.g. incisions, cosmetic surgery, etc.

Alternatively, wounds may be the result of other medical diseases or conditions, such as diabetes. Patients with diabetes may develop wounds such as ulcers (e.g. foot or other ulcers, and/or venous leg ulcers) due to poor circulation and/or high blood sugar (hyperglycemia) nerve damage. In such aspects, the wounds may be very slow healing or non-healing chronic wounds.

Other patients that are susceptible to slow-healing and/or chronic wounds include the elderly and patients who are immobile or who have limited mobility, such as paraplegics, quadraplegics and other bed-ridden or wheel-chair bound patients. For such patients, poor circulation may lead to thinning of the skin and susceptibility to skin breaches (wounding, bed sores, etc.) that would not typically occur, but for the lack of blood circulation. Subjects who are especially susceptible to problematic wounds include those who engage in/experience emergency procedures, smoking, severe obesity, altered immune function, malnutrition, low body temperature, long operation times, etc.

All such wounds, whether acute or chronic, or accidental or purposeful, may be successfully treated using the formulations disclosed herein.

In some aspects, the methods include additional measures prior to applying the present preparations (e.g. cleaning the wound, debridement, etc.). Further, the preparations disclosed herein may be used in conjunction with other wound treatment measures such as such as vacuum-assisted closure, skin grafts, hyperbaric oxygen therapy, and the like.

In further aspects, methods of accelerating re-epithelization (regeneration of epithelium), keratinization and closure of a wound, compared to control wounds, are provided. In other aspects, methods of accelerating, at the site of a wound, the generation of mature organized tissue with a characteristic perpendicular arrangement of newly produced blood capillaries, compared to control wounds. In further aspects, the methods do so while decreasing the production of inflammatory cells in or at the wound site, compared to control wounds.

It is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Representative illustrative methods and materials are herein described; methods and materials similar or equivalent to those described herein can also be used in the practice or testing of the present invention.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual dates of public availability and may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as support for the recitation in the claims of such exclusive terminology as "solely," "only" and the like in connection with the recitation of claim elements, or use of a "negative" limitations, such as "wherein [a particular feature or element] is absent", or "except for [a particular feature or element]", or "wherein [a particular feature or element] is not present (included, etc.) . . . ".

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

The invention is further described by the following non-limiting examples which further illustrate the invention, and are not intended, nor should they be interpreted to, limit the scope of the invention.

EXAMPLE

Materials and Methods

Thioctic acid and GA were procured from Sigma-Aldrich Corp (St. Louis, Mo., USA) and NATCO Pharma Limited (NATCO House, Hyderabad, India), respectively. All chemicals and solvents used were of analytical grade.

Preparation and Characterization of Thioctamer

Thioctamer was prepared by conjugation of GA and TA in a 1:1 molar ratio. TA was solvated in deionized water (with added of triethanolamine in a 1:1 molar ratio with the amount of TA). GA was dissolved separately in deionized water. The two aqueous solutions were mixed and then vortexed for 60 sec.

Thioctamer Zeta Potential and Particle Size Evaluation

The prepared thioctamer was assessed for zeta potential and particle size utilizing a Zetasizer Nano ZSP (Malvern Instruments Ltd., Malvern, UK).

Thioctamer Loaded Hydrogel Preparation

HPMC (hydroxy propyl methyl cellulose) was dispersed in distilled water at a 1.5% w/v concentration then thioctamer was added to the HPMC solution that was kept stirring using magnetic stirrer at ambient temperature. The hydrogels were kept for 24 h to swell at RT before additional experiments were conducted. Further, hydrogels of TA and GA were prepared separately applying the same procedure as for thioctamer hydrogel preparation.

Animals

Thirty 210-240 g male Wistar rats were provided by KAU's animal facility and were maintained on a 12-hr dark-light cycle at a temperature of 22 ±2° C. The animal care procedures were certified by Faculty of Pharmacy's Research Ethics Committee (PH-1443-09). Induction of diabetes in rats was carried out as formerly described, i.e. prior to the study, rats were intra-peritoneally injected with streptozotocin (50 mg/kg) for two weeks. Go Accu-Chek was utilized for assessing the level of fasting blood glucose (Roche, Mannheim, Germany) Moderate-diabetic rats with level of fasting blood glucose (200-300 mg/100 mL) were chosen for the experiment.

Animal Wounding and Treatment

Rats were anesthetized by xylazine and ketamine (10 mg/kg and 100 mg/kg, respectively IP injection). The dorsal surface was shaved, the skin was sterilized by povidone-iodine solution, and an excision circle (1 cm diameter) was made on dorsal surface. After the excision, the wounds were cleaned and dried using sterile saline solution and sterile pads, respectively. Subcutaneous injection of 2% solution of lidocaine hydrochloride having 1:80,000 epinephrine (4.4 mg/kg) was performed near the wound area to reduce pain. 5 Groups (6 rats, each) of wounded-diabetic rats were organized according to the treatment received on the wounded area: Group I received 1.5% w/v HPMC-based hydrogel (negative control); Group II received 1.5% w/v HPMC-based hydrogel preparation of 4.1 mg/g gel TA; Group III received 1.5% w/v HPMC-based hydrogel preparation of 12.5 mg/g gel GA; Group IV received 1.5% w/v HPMC-based hydrogel 16.6 mg/g gel Thioctamer complexes; Group V received 0.5 g Mebo™ ointment (positive control). All treatments were topically applied daily for a total of 10 days. The wounds were wrapped with sterile gauze dressings and changed daily. At days 0, 4, 7, and 10, wounds were photographed and assessed. Animals were sacrificed by beheading at the end of day 10 and the skin of wound area was cut out. From each animal, a part of the obtained skin was retained in 10% neutral formalin, while the other part was preserved at -80° C. for further analyses.

Measurement of Wound

% wound closure was estimated using equation (1), taking into account the wound diameter changes:

$$\% \text{ of wound closure} = \frac{\text{Wound diameter at day 0} - \text{Wound diameter on the last day}}{\text{Wound diameter at day 0}} \times 100 \quad \text{Equation (1)}$$

Histological Investigation

Wound tissues were preserved for 24 h in 10% neutral formalin, then dehydrated using serial concentrations of ethanol, passed through xylene as a clearing agent, and inserted in paraffin. Tissues' paraffin blocks were cut into 5 μm thickness that were rehydrated after dewaxing. Some sections were stained using E&H (eosin and hematoxylin), whereas the remaining were stained with MT (Masson's trichrome). Histological investigation was carried out by a pathologist without prior knowledge of the groups'treatment. On the basis of the abundance/degree of inflammatory cell infiltration, proliferation of fibroblasts, deposition of collagen, angiogenesis, tissue granulation, and re-epithelization, scores were assigned in a range from - to +++.

Immuno-Histochemical Estimation of TNF-α and IL-6 Expression

Each tissue section was treated by drying, deparaffinization, rehydration, and boiling in citrate buffer for 10 min at pH 6.0. A Tissue and Cell Staining Rabbit Kit having secondary antibody, blocking solution, and DAB (3,3'-diaminobenzidine) (R&D Systems, Minneapolis, MN, USA) was utilized. After that, the sections were incubated for 120 min in 5% bovine serum albumin followed by overnight incubation at 4° C. with anti-TGF-β1 or anti-VEGF-antibodies (1 μg/ml). After washing, slides were kept at RT for 60 min with the biotinylated secondary antibody and then were washed with PBS having 0.5% Tween™ 20. Thereafter, addition of DAB and observation of color development were performed using a 1000 Nikon SMZ light microscope equipped with a DS-Fi1Nikon digital camera (Tokyo, Japan). Image analysis was done using ImageJ analysis software (ImageJ, 1.46a, NIH, USA).

Statistical Analysis

Data are shown off as mean ±SD. ANOVA (one-way analysis of variance) followed by Tukey's post hoc test were utilized for multiple comparisons. All analyses were done using version 8.0 GraphPad Prism software®. Only two-tailed p values <0.05 were regarded as statistically significant.

Results

Preparation and Characterization of Thioctamer

Figure 2:
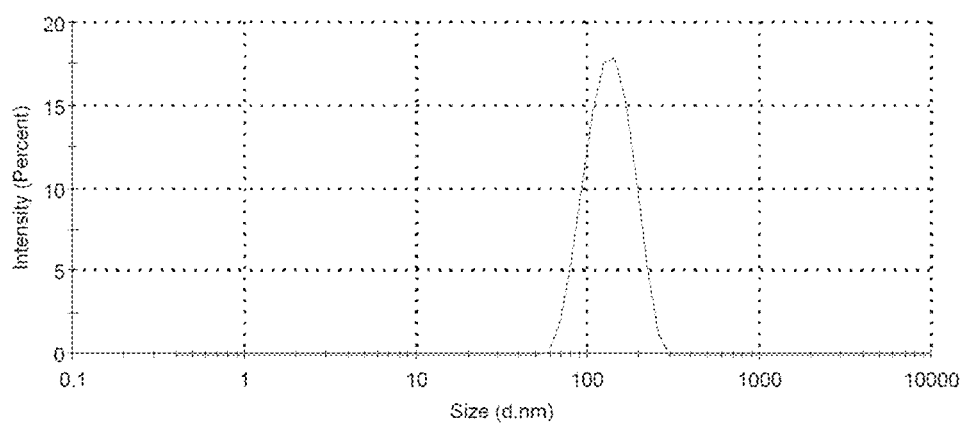
FIG. 2. Thioctamer particle size as measured with the particle size analyzer.
Figure 3A:
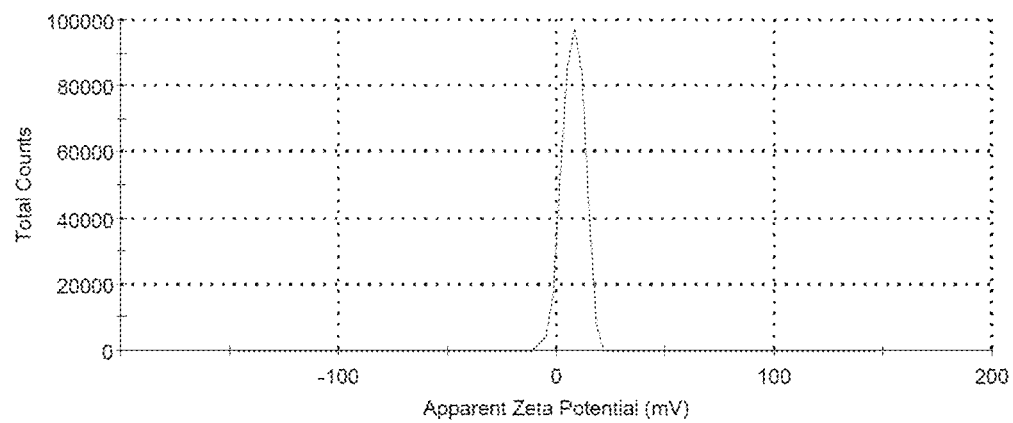
FIGS. 3A-C. Zeta potential values of thioctamer (A), TA (B) and GA (C).
Figure 3B:
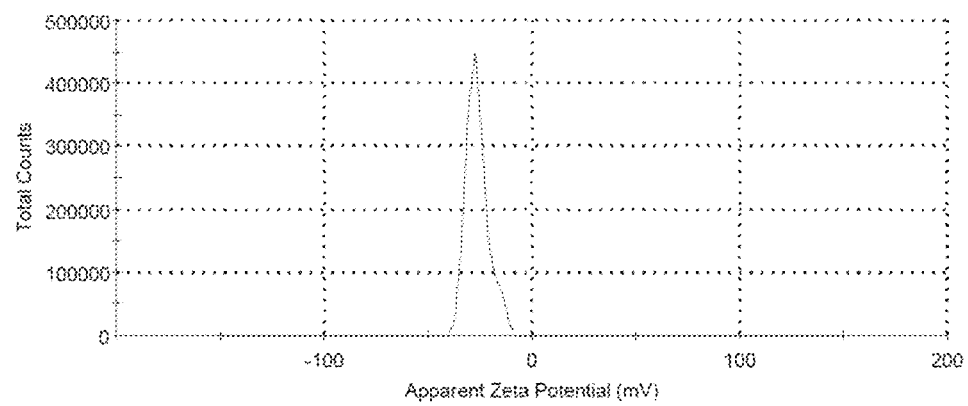
Figure 3C:
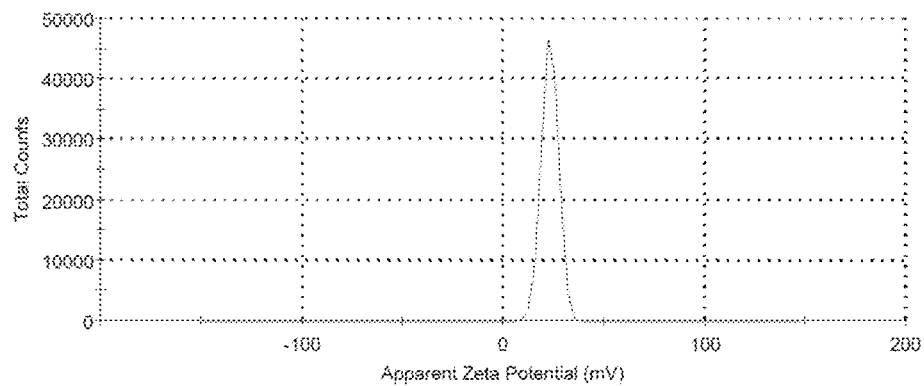

Thioctamer was prepared in GA: TA 1:1 molar ratio. The results demonstrated a thioctamer particle size of 137±21.4 nm (Z-average 166.4 nm) with PDI of 0.235 (FIG. 2). Thioctamer showed a positive zeta potential value of 7.43±4.95 mV (FIG. 3A) when compared with the negative zeta potential value of TA of -26.6±5.39 (FIG. 3B) and the positive zeta potential value of GA 23±4.2 mV (FIG. 3C).

These results revealed that thioctamer showed a net positive charge after the conjugation of TA (negatively charged) and GA (positively charged).

Assessment of Wound Healing

Figure 4A:
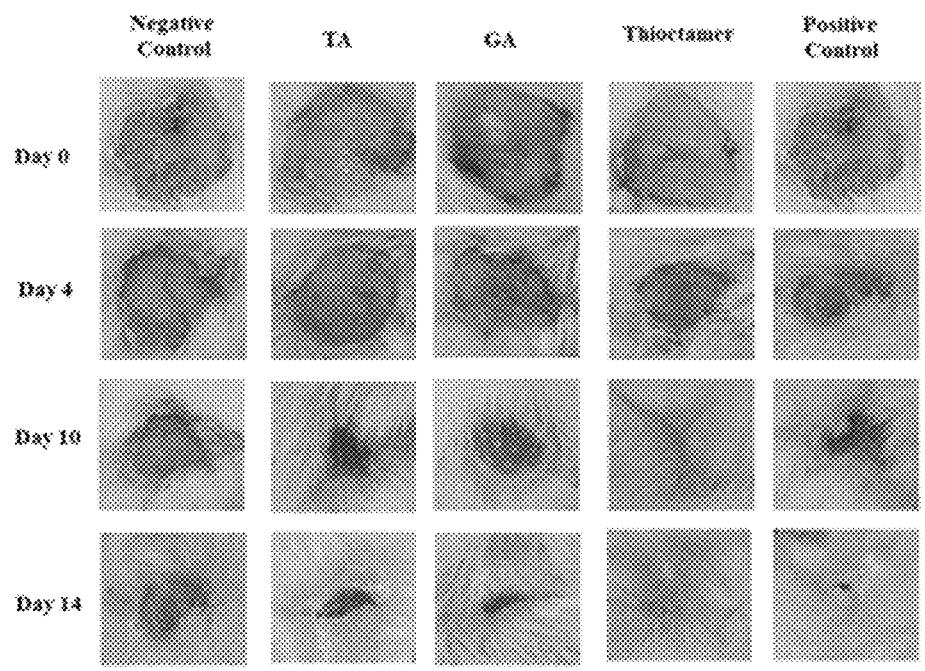
FIGS. 4A and B. (A) Wound closure in diabetic rats at day 0, 4, 10, and 14 in the 5 experimental groups. (B) Wound contraction % at day 10. Data are shown as mean (n=6)±SD. # Significantly varied vs negative control; a Significantly varied vs TA; $ Significantly varied vs GA; * Significantly varied vs Positive control FIG. 5. Histopathological effects of thioctamer loaded gel on wound healing on day 10. MT=Masson's trichrome (scale bar=50 μm); H&E=hematoxylin and eosin (scale bar=100 μm).
Figure 4B:
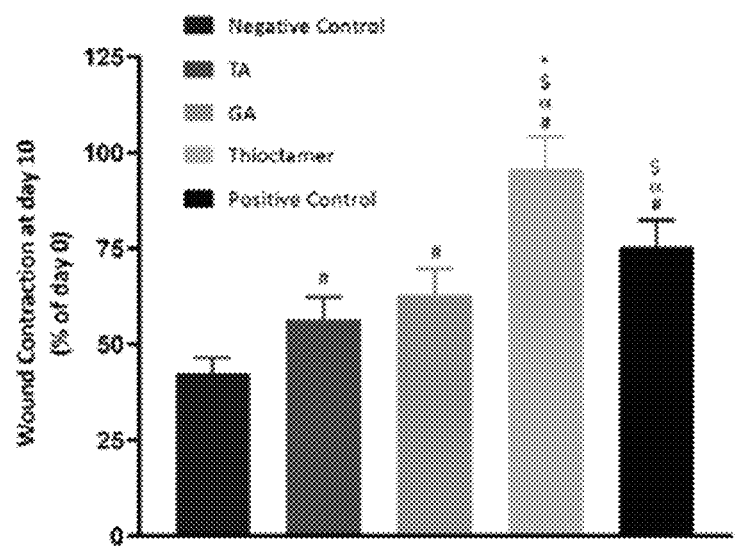

At day 7, wounds of diabetic rats administered thioctamer preparation showed almost entire healing (95.6±8.6%). Meanwhile, % of wound contraction in animals treated with of TA or GA groups exhibited values amounting to 56.5±5.8% and 62.6±7.1%, respectively. It is noteworthy that the thioctamer preparation significantly expedited wound healing compared to the positive control (FIG. 4). This superior wound healing activity of thioctamer was still observed even at day 10.

Histopathological Investigation

Figure 5:
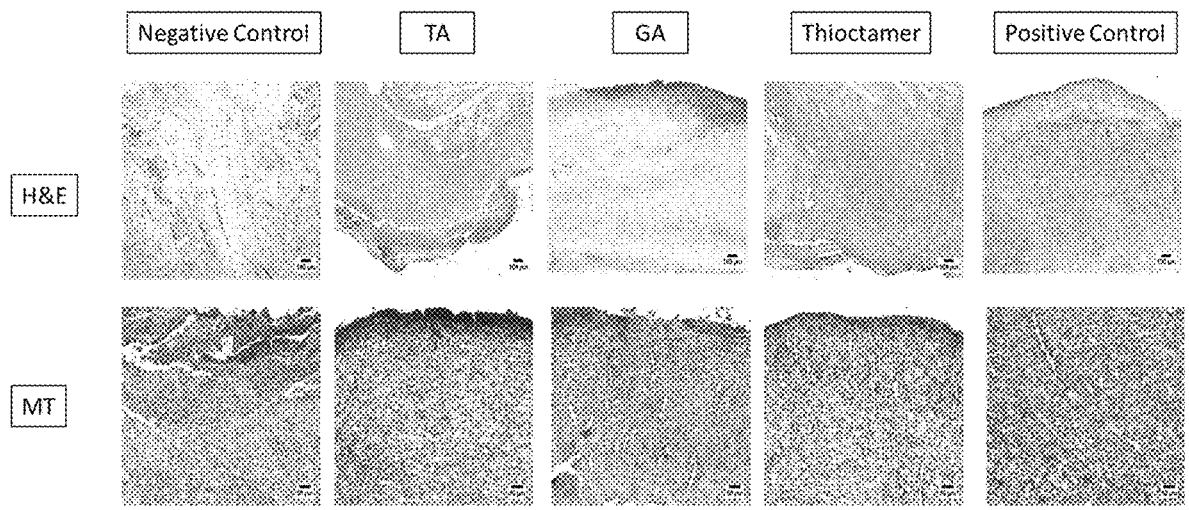

The data observed when assessing the ability of thioctamer preparation to expedite wound healing activity were further confirmed by histological investigation. Staining with hematoxylin and eosin or Masson's trichrome of wound tissues collected on day 10 revealed that the negative control group animals demonstrated delayed healing signs as well as poor epidermal remodeling and re-epithelization (FIG. 5). The wound gap was occupied by severely inflamed granulation tissue with excessive edema and hemorrhages in the wound base. Transmigration of heavy neutrophilic infiltration was recognized in the wound covering that was accompanied by abundant eosinophilic, karyorrhectic debris and necrotic crust. Tissues collected from TA or GA treated animals possessed to a certain extent moderate healing rate as re-epithelization deeply expanded into the center of the wound. The newly produced epithelium was vacuolated with early keratinization. The highest healing rate was noted for the thioctamer treated animals, where the wound surface was nearly fully covered by regenerated epithelium with keratinization and few inflammatory cells were observed. Wounds were filled with mature organized tissue with its characteristic perpendicular arrangement of the newly produced blood capillaries over the formed fibrous tissue. The positive control group displayed better healing as inflammation was prohibited and epidermal remodeling was noted (FIG. 5). The histological characteristics are presented in Table 1.

TABLE 1

Histological assessment of day 10 wound healing in animals receiving topical application of TA, GA, or Thioctamer nanocomplex.

| | IC | FP | CD | GT | Ang | RE |
|---|---|---|---|---|---|---|
| Negative Control | ++++ | ++ | + | + | − | − |
| TA | +++ | ++ | ++ | ++ | + | ++ |
| GA | +++ | ++ | ++ | ++ | + | ++ |
| Thioctamer | + | ++++ | ++++ | ++++ | +++ | ++++ |
| Positive Control | ++ | ++ | +++ | +++ | ++ | ++ |

FP = Fibroblast proliferation; IC = Inflammatory cell infiltration; GT = Granulation tissue; CD = Collagen deposition; RE = Re-epithelization; Ang = Angio-genesis.

The greatest vascular alteration and infiltration of inflammatory cells were observed in the negative control group, whereas improvement of angiogenesis and inflammation process were noticed in the other groups. As indicated by the scores of histopathological lesions, improvement in epidermal remodeling in positive control group animals as well as of TA, GA, or thioctamer groups were evident relative to the negative control group. Treatment with the thioctamer nanocomplex gave the highest score for angiogenesis, collagen deposition, and re-epithelization compared to the other groups and the positive control group.

Immunohistochemical Assessment of IL-6 and TNF-α Expression

Figure 6A:
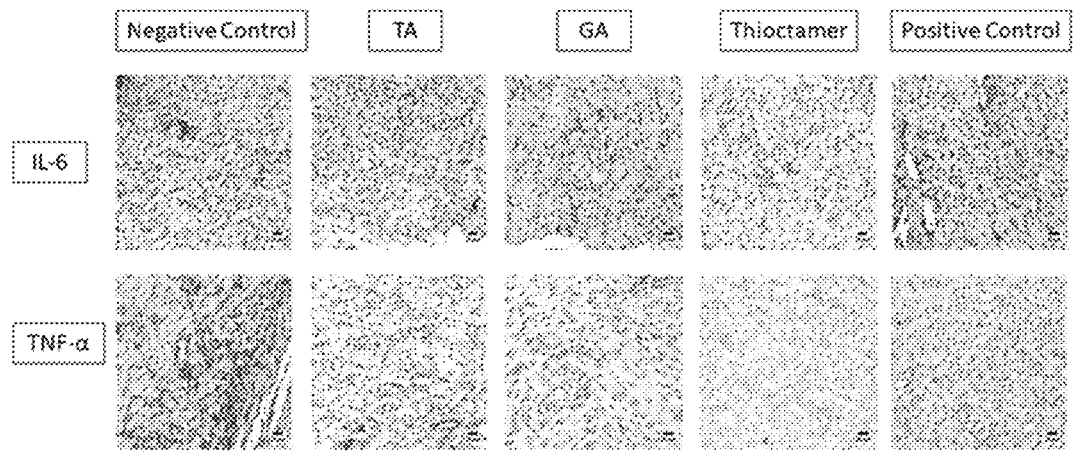
FIGS. 6A-C. Effect of TA, GA, or thioctamer nanocomplex on IL-6 and TNF-α expression in diabetic rats wounded skin. A, Immunohistochemical assessment; B, graphical representation of the data for IL-6; C, graphical representation of the data for TNF-α. Data are shown as mean ±SD, (n=6). # Significantly varied vs negative control; αSignificantly varied vs TA; Significantly varied vs GA; * Significantly varied vs Positive control.
Figure 6B:
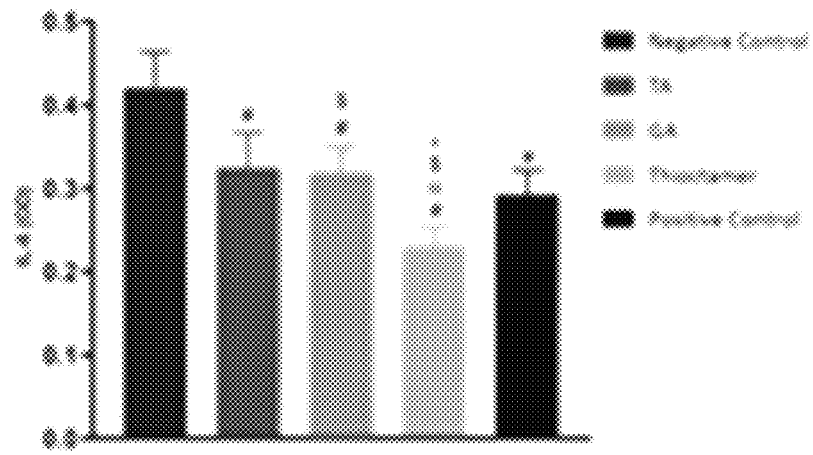
Figure 6C:
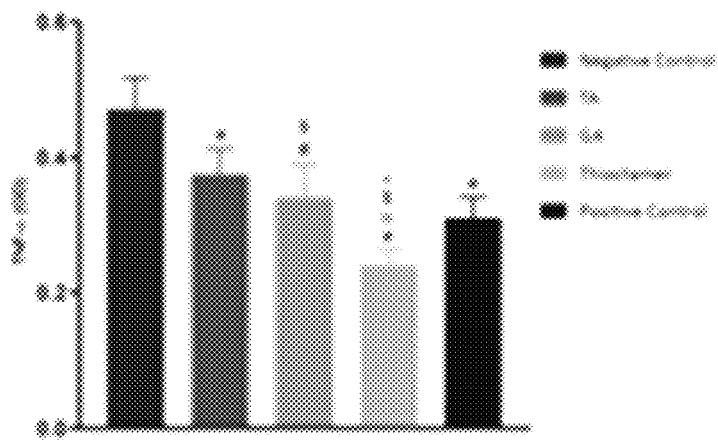

The data in FIG. 6A (upper panel) showed that the topical treating of wounded skin tissues with TA, GA, or thioctamer remarkably prohibited IL-6 expression by 0.324±0.043, 0.318±0.033, and 0.23±0.024, respectively, as compared to sections obtained from the negative control group animals (0.42±0.044). Similarly, TNF-α expression was significantly inhibited by TA, GA and thioctamer by values amounting to 0.374±0.039, 0.34±0.05 and 0.241±0.025, respectively, as compared to negative control (0.47±0.048) (FIG. 6A, Lower Panel). FIGS. 6B and 6C show the data for IL-6 and TNF-α, respectively, in graphical form.

While the invention has been described in terms of its several exemplary embodiments, those skilled in the art will recognize that the invention can be practiced with modification within the spirit and scope of the appended claims. Accordingly, the present invention should not be limited to the embodiments as described above but should further include all modifications and equivalents thereof within the spirit and scope of the description provided herein.

We claim:

1. A method of treating an acute wound in a subject in need thereof, comprising
    applying to the acute wound a hydrogel comprising thioctamer nanospheres comprised of glatiramer acetate (GA) and thioctic acid (TA), said nanospheres having a size of from 115-160 nm, thereby treating the acute wound.

2. The method of claim 1, wherein the thioctamer nanospheres are present in a pharmaceutical formulation comprising at least one physiologically acceptable carrier.

3. The method of claim 1, wherein the subject is diabetic.

4. The method of claim 3, wherein the wound is a diabetic ulcer.

5. The method of claim 1, wherein the step of applying results in acceleration of one or more of: closure of the wound, re-epithelization of the wound, keratinization of the wound, generation of mature organized tissue with a characteristic perpendicular arrangement of newly produced blood capillaries and a reduction of inflammatory cells in or at the wound site, compared to a control wound that is not treated with the thioctamer nanospheres.

6. The method of claim 1, wherein the hydrogel contains 10-25 mg/g thioctamer nanospheres.

* * * * *